(12) United States Patent
Hohlbein

(10) Patent No.: US 7,823,243 B2
(45) Date of Patent: Nov. 2, 2010

(54) TOOTHBRUSH

(75) Inventor: Douglas Hohlbein, Pennington, NJ (US)

(73) Assignee: Colgate-Palmolive Company, New York, NY (US)

( * ) Notice: Subject to any disclaimer, the term of this patent is extended or adjusted under 35 U.S.C. 154(b) by 866 days.

(21) Appl. No.: 11/113,769

(22) Filed: Apr. 25, 2005

(65) Prior Publication Data

US 2005/0188489 A1 Sep. 1, 2005

Related U.S. Application Data

(63) Continuation of application No. PCT/US03/34589, filed on Oct. 30, 2003.

(60) Provisional application No. 60/423,254, filed on Nov. 1, 2002.

(51) Int. Cl.
A46B 5/00 (2006.01)
A46B 9/04 (2006.01)

(52) U.S. Cl. .................... 15/167.1; 15/172

(58) Field of Classification Search ........... 15/167.1, 15/172
See application file for complete search history.

(56) References Cited

U.S. PATENT DOCUMENTS

| | | | |
|---|---|---|---|
| 958,371 A | 5/1910 | Danek | |
| 2,241,876 A | 5/1941 | Cohen | |
| 2,706,825 A | 4/1955 | Blakeman | |
| 4,637,660 A | 1/1987 | Weihrauch | |
| 4,691,404 A * | 9/1987 | Tarrson et al. | 15/167.1 |
| 5,390,984 A | 2/1995 | Boucherie et al. | |
| 5,396,678 A * | 3/1995 | Bredall et al. | 15/167.1 |
| 5,533,791 A | 7/1996 | Boucherie | |
| 5,609,890 A | 3/1997 | Boucherie | |
| 5,625,916 A | 5/1997 | McDougall | |
| 5,628,082 A | 5/1997 | Moskovich | |
| 5,651,158 A | 7/1997 | Halm | |
| RE35,941 E | 11/1998 | Stansbury, Jr. | |
| 5,903,949 A | 5/1999 | Halm | |
| 5,926,900 A | 7/1999 | Bennett | |
| 5,970,564 A * | 10/1999 | Inns et al. | 15/201 |
| 6,073,299 A | 6/2000 | Hohlbein | |
| 6,088,870 A * | 7/2000 | Hohlbein | 15/167.1 |
| 6,101,659 A | 8/2000 | Halm | |
| 6,108,852 A * | 8/2000 | Vrignaud | 15/167.2 |
| 6,357,074 B1 | 3/2002 | Weihrauch | |

(Continued)

FOREIGN PATENT DOCUMENTS

CN 2205663 Y 8/1995

(Continued)

OTHER PUBLICATIONS

Supplementary European Search Report from the European Patent Office for corresponding European Patent Application No. EP 03781565.1.

*Primary Examiner*—Randall Chin
(74) *Attorney, Agent, or Firm*—Amy M. Fernandez

(57) ABSTRACT

A toothbrush with a flexible head is disclosed. At least the head of the toothbrush may be manufactured by in-molded technology. A blend of thermoplastic elastomer and polypropylene is used to impart added flexibility to the head. That flexibility is further enhanced by the tapered profile of the head. Cleaning elements may be secured in place during manufacture using in-molded techniques or staples.

16 Claims, 1 Drawing Sheet

U.S. PATENT DOCUMENTS

| | | |
|---|---|---|
| 6,408,476 B1 | 6/2002 | Cann |
| 6,502,272 B1 * | 1/2003 | Fox et al. .................. 15/167.1 |
| 6,601,272 B2 * | 8/2003 | Stvartak et al. ............. 16/430 |
| 6,675,428 B2 * | 1/2004 | Halm ....................... 15/167.1 |
| 2005/0193512 A1 * | 9/2005 | Moskovich et al. ........ 15/167.1 |

FOREIGN PATENT DOCUMENTS

| | | |
|---|---|---|
| DE | 199 32 377 A1 | 8/2001 |
| EP | 0 577 656 | 5/1997 |
| EP | 0 756 837 | 6/1997 |
| GB | 2 050 156 A | 1/1981 |
| JP | 2002095526 A | 4/2002 |
| RU | 2 048 132 C1 | 11/1995 |
| WO | WO96/02165 | 1/1996 |
| WO | WO 97/07707 | 3/1997 |
| WO | WO 98/12948 A1 | 4/1998 |
| WO | WO 99/17915 A1 | 4/1999 |

* cited by examiner

TOOTHBRUSH

CROSS-REFERENCE TO RELATED APPLICATIONS

This is a continuation of International Application PCT/US03/34589, filed Oct. 30, 2003, which claims priority from U.S. Application 60/423,254, filed Nov. 1, 2002, both of which are incorporated by reference herein in their entirety.

BACKGROUND OF THE INVENTION

The present invention is directed to a toothbrush, either manual or powered, which includes a handle and a head. Cleaning elements are mounted to the head such as tufts of bristles and/or elastomeric wipers. When toothpaste is applied to the cleaning elements the user inserts the head into the mouth and brushes the teeth in a known manner.

The head of a conventional toothbrush usually has a flat or slightly altered surface to which cleaning elements are attached. Usually the cleaning elements are strands of plastic material(s) formed into tufts, bundles or other groupings. A goal of many toothbrushes is to accommodate the cleaning element profile to that of the teeth being cleaned. Achieving that goal is complicated by the difficulty in matching a toothbrush profile to the complex surface of a typical set of human teeth. The latter generally lie in a "C" shaped curve which presents the need for a brush to address a convex outer curve and a concave inner curve. In addition, the toothbrush should be capable of cleaning irregularities on the tooth surface as well as the interproximal area between teeth.

Various approaches have been taken in the prior art to accommodate the complex shape of the human mouth and the attendant difficulties in cleaning teeth and gums within the mouth. One approach to this problem is provision of a flexible toothbrush head.

Blakeman U.S. Pat. No. 2,706,825 issued Apr. 26, 1955 discloses a replaceable bristle head for a toothbrush. The flexible head undulates in a manner so that rows of bristles move in a direction aligned with the axis of the toothbrush handle.

U.S. Pat. No. 5,651,158 issued Jul. 29, 1997 to Hans Halm discloses a toothbrush handle with a segmented head wherein adjoining segments are linked by an elastomeric material. The segments are primarily oriented transverse to the longitudinal axis of the toothbrush but may also be oriented parallel to that axis.

U.S. Pat. No. 6,408,476 discloses another form of segmented toothbrush head with transverse grooves and an elastomeric portion joining the segments. A method of manufacturing this head is also disclosed.

The use of elastomeric material within folds of a toothbrush handle is the subject of U.S. Pat. No. 5,903,949.

International Publication Number WO96/02165 dated Feb. 1, 1996 discloses a resiliently flexible bristle-bearing toothbrush head containing bristles with a generally concave surface. The head, being flexible, can flex under the action of tooth brushing to accommodate the varying profiles of users' teeth. Grooves transverse or parallel to the longitudinal axis of the toothbrush which are filled with elastomeric material permit flexure along the length or across the breath of the head (pages 4-5).

A tip region of a toothbrush head is flexibly mounted to the rigid balance of the head in the disclosure of International Publication Number WO 97/07707 dated Mar. 6, 1997. A flexible plastic material forms the link (hinge) which connects the two parts of the head (pages 2-3). In use, the tip region of the head can fold backwards toward the rigid balance of the head, thereby enabling the head to better accommodate itself to the curved shape of the user's teeth.

Another flexible toothbrush head is disclosed n European Patent Specification No. EP 0577 656 B1 published May 4, 1997.

SUMMARY OF THE INVENTION

A common theme among the aforementioned approaches to providing a flexible head is the use of different materials throughout the head to achieve the desired flexibility. Most of the above cited art use elastomeric materials at joints in the head structure to provide that flexibility. This invention proposes to achieve flexibility while using a homogeneous material for the head, rather than separate portions of the head with varying physical properties. This approach offers considerable simplification of a flexible toothbrush head assembly.

The preferred material for forming the head has sufficient rigidity to maintain the structure of the head and retain the cleaning elements in place within the head while still offering the desired flexibility. This desired mix of properties can be achieved by blending two or more materials prior to molding. A preferred blend uses a large percentage (up to about 50%) of a thermoplastic elastomer (TPE) with polypropylene. The percentages of the respective components would be governed by the geometry of the head, with a thinner head generally needing less TPE for flexibility.

Because a softer material is used in the head, retention of cleaning elements in the head may require special attention. Therefore, special care should be taken in staple insertion to properly anchor the cleaning elements. Alternatively, groups or tufts of cleaning elements can be secured in the flexible head of this invention using the injection molding technique (IMT) for placement and securement of toothbrush bristles. In the IMT process, the bristles are preferably attached during formation of the toothbrush handle, or at least during formation of the head.

DETAILED DESCRIPTION

The toothbrush 10 of this invention includes handle 12 and head 14. Head 14 is preferably formed of a flexible plastic material, comprising a blend of thermoplastic elastomers such as those sold under the KRATON® trademark, and polypropylene. This blend, and those similar to it, provide a unique combination of flexibility and structural integrity for the toothbrush head.

Figure 3:
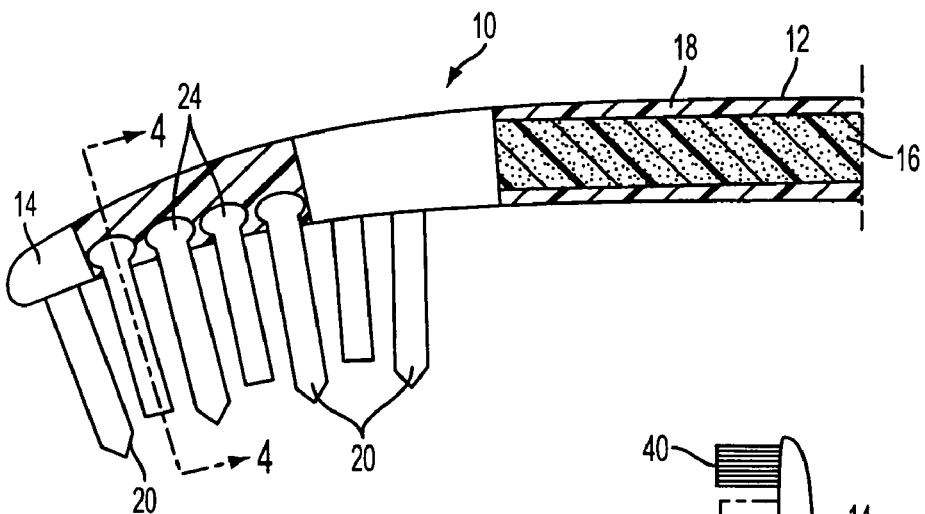
FIG. 3 is a fragmental side elevational view, partially broken away to show flexible encasement of bristles in the toothbrush head.

The desired flexibility of head 14 is also a function of its shape and thickness. Thus, as shown in FIG. 3, the thickness of head 14 may be gradually reduced or tapered toward the distal end of the toothbrush 10 to improve the flexibility of the head 14.

While it is an object of this invention to provide a flexible head 14, the handle 12 typically should be more rigid so that the user can control the force of the toothbrush 10 on the user's teeth. To accomplish that goal, it is desirable to include a more rigid plastic in at least a portion of the handle 12 of toothbrush 10. To achieve this marriage of a flexible head and relatively rigid handle, several approaches can be taken. The flexible blend of KRATON® and polypropylene can be used as a core material 16 for the handle surrounded by a more rigid plastic shell 18. Conversely, the core 16 can be formed of a more rigid material and the shell 18 formed from the TPE and polypropylene blend. As shown in FIG. 3, the latter embodiment provides a soft "feel" to the handle and is thus a desirable feature in most applications.

Figure 2:
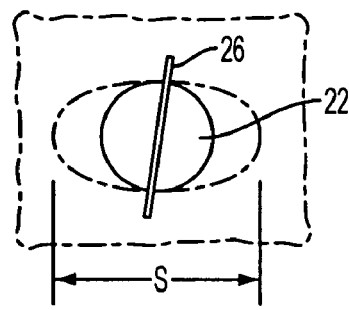
FIG. 2 is a schematic fragmental top plan view of a single tuft of bristles placed in the hole of the flexible head of this toothbrush.

The use of the more flexible blend material for head 14 does present some special issues regarding placement and retention of cleaning elements 20 in head 14. During flexure of flexible head 14, the holes 22 in head 14 which hold the cleaning elements 20 may be widened or expanded as illustrated in FIG. 2. More specifically, one dimension of the hole 22 may be enlarged as represented by the distances shown in FIG. 2. That enlargement of hole 22 could loosen the hold on the tufted end 24 of cleaning elements 20 inserted in head 14. To minimize the chance that any group of cleaning elements 20 might pull out of hole 22 in head 14, it is desirable to carefully orient staples 26 used to secure the tufted end of cleaning elements 20 in hole 22.

Figure 1:
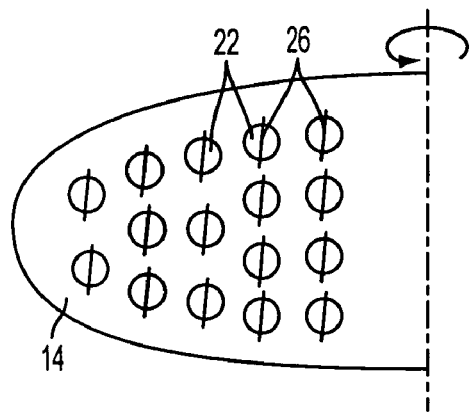
FIG. 1 is a fragmental top plan view of a toothbrush head showing placement of a group of bristles (tufts) and staples holding the bristles in the head.

Thus, as shown in FIGS. 1 and 2, if head 14 flexes along a line perpendicular to the longitudinal axis of toothbrush 10 as shown by the arrow in FIG. 1, the staples 26 are preferably similarly aligned with the flex axis. Thereby, there is minimal movement of the staples during flexure.

An alternative means for improving retention of cleaning elements 20 in the flexible head 14 is use of the IMT process. Descriptions of that process used for the manufacture of toothbrushes are found in U.S. Pat. Nos. 5,390,984; 5,533,791 and 5,609,890, the disclosures of which are incorporated herein by reference.

Figure 4:
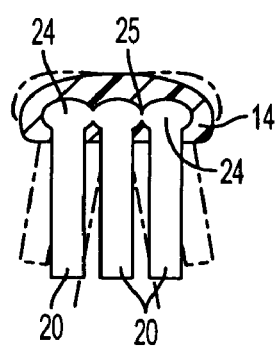
FIG. 4 is a cross sectional end view taken along line 4-4 of FIG. 3 with phantom outline of the bristles movement with the flexible head.

In the IMT process, the tufted ends 24 of cleaning units 20 are held in place as the head 14 is formed. The rounded ends 24 assume a mushroom shape (See FIGS. 3 and 4) which is essentially surrounded by the TPE/polypropylene blend used to form head 14. This mushroom shape helps to hold the tufted ends 24 of cleaning elements 20 in place, even when one axis of the head 14 is stretched. To further improve retention of cleaning elements 20 in head 14, the IMT process can be operated with localized heating to partially melt the tufted ends 24 of cleaning elements 20 so that a bridge 25 is formed between ends 24. As illustrated in FIG. 4, this bridge 25 integrates the various groupings of cleaning elements 20 at the ends 24. The flexible head 14 is then molded around the bridge 25. This substantially improves retention of cleaning elements 20 in head 14. This bridging is particularly effective in holding cleaning elements 20 in place where the head 14 is flexed in a direction where the cleaning elements move laterally relative to the longitudinal axis of the toothbrush 10, as illustrated in FIG. 4.

Any suitable form of cleaning elements may be used as the cleaning elements 20 in the broad practice of this invention. The term "cleaning elements" is intended to be used in a generic sense which could include conventional fiber bristles or massage elements or other forms of cleaning elements such as elastomeric fingers or walls arranged in a circular cross-sectional shape or any type of desired shape including straight portions or sinusoidal portions.

It is to be understood that the specific illustration of the cleaning elements is merely for exemplary purposes. The invention can be practiced with various combinations of the same or different cleaning element configurations (such as stapled or in-molded technology bristles, etc.) and/or with the same bristle or cleaning element materials (such as nylon bristles, spiral bristles, rubber bristles, etc.) Similarly, while FIGS. 3-4 illustrate the cleaning elements to be generally perpendicular to head 14, some or all of the cleaning elements may be angled at various angles with respect to the outer surface of head 14. It is thereby possible to select the combination of cleaning element configurations, materials and orientations to achieve specific intended results to deliver additional oral health benefits, like enhanced cleaning, tooth polishing, tooth whitening and/or massaging of the gums.

This invention may also be practiced where the head 14 includes one or more power or electrically operated movable sections carrying cleaning elements.

Figure 5:
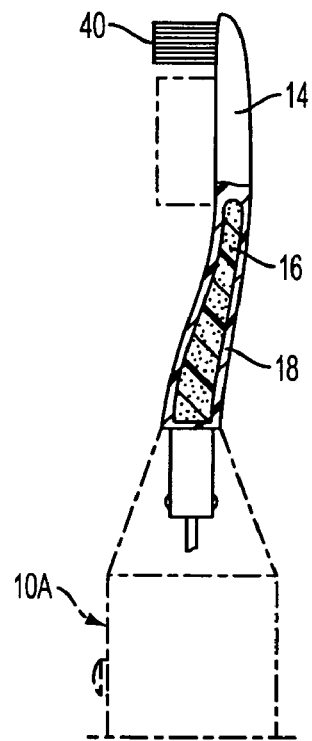
FIG. 5 is a fragmental side elevational view of a power toothbrush having a removable flexible head.

FIG. 5 illustrates a toothbrush 10A which includes a power driven movable disc or section 40 having cleaning elements. The movable section 40 could be oscillated rotationally such as by using the type of drive mechanism shown in U.S. Pat. No. 5,625,916, or could move in and out using the type of drive mechanism shown in U.S. Pat. No. Re35,941; all of the details of both patents are incorporated herein by reference thereto. Alternatively, the other types of drives referred to above could move section 40 in other manners and directions. Although FIG. 5 shows movable section 40 to be at one end of the head, the movable section(s) could be located at any desired location on the head.

What is claimed is:

1. A toothbrush comprising:
   a handle;
   a head secured to the handle and having a flexural axis, the entirety of the head formed only of a homogeneous blended material, the entirety of the head having greater flexibility than the handle;
   a plurality of cleaning elements secured to the head; and
   wherein the handle includes a first portion formed from the homogeneous blended material and a second portion formed from a rigid material, the first portion of the handle being integrally formed with the head.

2. The toothbrush of claim 1 wherein said first portion is at least partially surrounded by said second portion of the handle, the first portion forming a core of said handle.

3. The toothbrush of claim 1 wherein said first portion surrounds said second portion, said second portion forming a core of the handle.

4. The toothbrush of claim 1 wherein the homogeneous blended material is a blend of a thermoplastic elastomer and polypropylene.

5. The toothbrush of claim 1 wherein the head has a proximal end and a distal end, the proximal end having a greater thickness than a thickness of the distal end to improve flexibility of the head.

6. The toothbrush of claim 1 wherein the cleaning elements comprise a first end embedded in the head, and wherein for each of the cleaning elements, the first end is melted to at least one other first end of an adjacent cleaning element.

7. The toothbrush of claim 1 further comprising:
   the cleaning elements extending from recesses in the head; and
   staples securing the cleaning elements in the recesses in the head, wherein all of the staples are substantially aligned with the flexural axis of the toothbrush head.

8. The toothbrush of claim 1 further comprising:
wherein the homogeneous blended material is a blend of a thermoplastic elastomer and polypropylene;
wherein the head has a proximal end and a distal end, the proximal end having a greater thickness than a thickness of the distal end to improve flexibility of the head;
the cleaning elements extending from recesses in the head; and
staples securing the cleaning elements in the recesses in the head, wherein all of the staples are substantially aligned with the flexural axis of the toothbrush head.

9. The toothbrush of claim 8 wherein said first portion is at least partially surrounded by said second portion of the handle, the first portion forming a core of said handle.

10. The toothbrush of claim 8 wherein said first portion surrounds said second portion, said second portion forming a core of the handle.

11. A toothbrush comprising:
a handle;
a head secured to the handle and having a flexural axis, wherein the entirety of the head is formed only of a flexible homogeneous blended material;
a plurality of cleaning elements extending from recesses in the head; and
staples embedded in the flexible homogeneous blended material that secure the cleaning elements to the head, wherein all of the staples are substantially aligned with the flexural axis of the head.

12. The toothbrush of claim 11 wherein the entirety of head has a greater flexibility than the handle.

13. The toothbrush of claim 11 wherein the head comprises a proximal end having a first thickness and a distal end having a second thickness, the first thickness being greater than the second thickness.

14. The toothbrush of claim 11 wherein the handle includes a first portion formed from the homogeneous blended material and a second portion formed from a rigid material, the first portion of the handle being integrally formed with the head.

15. The toothbrush of claim 14 wherein said first portion is at least partially surrounded by said second portion of the handle, the first portion forming a core of said handle.

16. The toothbrush of claim 14 wherein said first portion surrounds said second portion, said second portion forming a core of the handle.

* * * * *